United States Patent [19]

Zinnes et al.

[11] 4,154,735
[45] May 15, 1979

[54] BIS 2-[(DIALKYLAMINO)METHYL]INDOLES

[75] Inventors: Harold Zinnes, Rockaway; Neil A. Lindo, New Providence, both of N.J.

[73] Assignee: Warner-Lambert Company, Morris Plains, N.J.

[21] Appl. No.: 903,637

[22] Filed: May 8, 1978

[51] Int. Cl.$^2$ .................. C07D 403/12; A01N 9/12; A61K 31/40

[52] U.S. Cl. ........................ 260/326.12 R; 424/274; 260/326.9

[58] Field of Search .......................... 260/326.12 R

[56] References Cited

PUBLICATIONS

Fontana et al., Chem. Abs. 86, 16928v, (1975).

Primary Examiner—Mark L. Berch
Attorney, Agent, or Firm—David B. Ehrlinger; Frank S. Chow; Stephen Raines

[57] ABSTRACT 3,3'-Thiodimethylenebis 2-[(dialkylamino)methyl]indole compounds having in free base form the formula

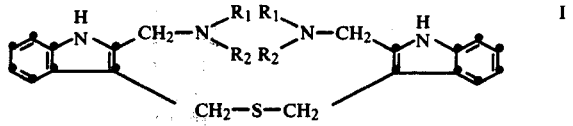

where $R_1$ and $R_2$ are lower alkyl groups. The compounds of this invention exhibit antifungal and CNS depressant properties and can be used as antifungal agents or CNS depressant agents.

5 Claims, No Drawings

BIS 2-[(DIALKYLAMINO)METHYL]INDOLES

SUMMARY AND DETAILED DESCRIPTION

The present invention relates to 3,3'-thiodimethylenebis 2[(dialkylamino)methyl]indole compounds having the formula

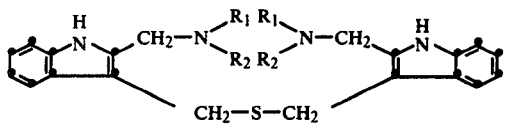

and acid addition salts thereof, where $R_1$ and $R_2$ are lower alkyl groups, that is, straight- or branched-chain alkyl groups of 1 to 6 carbon atoms such as methyl, ethyl, propyl, isopropyl, n-butyl, n-amyl, n-hexyl, and 2,3-dimethylbutyl.

According to the invention, compounds having formula I are prepared by reacting a quaternary salt of 2-alkyl 1,2,3,4-tetrahydropyrrolo[3,4-b]indole having the formula

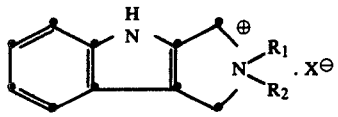

with thiourea in an aqueous alkaline medium, where $R_1$ and $R_2$ have the above-described meaning, and X is a halide, sulfate or sulfonate anion. The starting quaternary salt is prepared by treatment of the corresponding free base with alkyl halide, and the free base is prepared by known procedures such as those described by Southwick et al., J. Org. Chem. 25, 1133 (1960), which description is incorporated herewith by reference.

The compounds of the invention exist in free base form and pharmaceutically acceptable acid addition salt form. Such salts include, for example, salts formed with acids such as hydrochloric, sulfuric, nitric, and acetic acid and the like.

The compounds of the invention possess antifungal properties and central nervous system depressant properties. For example, the compound of formula I where $R_1$ and $R_2$ each represent methyl typically causes pronounced central depression when administered intraperitoneally to rodents such as the mouse at acute doses ranging from 10 to 100 mg./kg. of body weight. As another example, the same compound is fungistatic in vitro against *C. albicans* at 125 mcg./ml. and against *T. mentagrophytes* at 62.5 mcg./ml. The compounds in suitable unit dose form can be used as topical antifungal agents or oral or parenteral CNS depressant agents. The precise dosage and dosage regimen can be selected and varied using any of a variety of conventional formulations, depending on the mode of administration and the condition being treated, based on art-recognized practice.

The invention is illustrated by the following examples.

EXAMPLE 1

2-Methyl 1,2,3,4-tetrahydropyrrolo[3,4-b]indole methiodide (9.4 g.) was decolorized with charcoal in 600 ml. of boiling water. Thiourea (3.4 g.) in 40 ml. of 1.0 N aqueous sodium hydroxide solution was added to this. After about 5 minutes' reflux, a solid appeared. Refluxing was continued 3.5 hours, after which the mixture was cooled and extracted with ether. The combined extracts were dried and concentrated. The residual product, 3,3'40 -thiodimethylene-bis (N,N-dimethyl-1H-indole-2-methanamine), after trituration with methanol and recrystallization from methanol melts at 156°-9° C. with decomposition.

Calculated for $C_{24}H_{30}N_4S$: C-70.90; H-7.44; N-13.78; S-7.89.

Found: C-70.99; H-7.27; N-13.76; S-8.13.

The corresponding hydrochloride salt is obtained by dissolving the free base in ether, treating the solution with dry hydrogen chloride until precipitation of the product is complete, and isolating the product. The hydrobromide and sulfate are obtained by treating the free base in ether solution with dry hydrogen bromide or with sulfuric acid.

Following the procedure of Example 1 but replacing the quaternary salt starting material with an equivalent amount of a different alkyl substituted quaternary salt starting material provides other compounds of the invention as follows:

|     | Starting Material | Product |
| --- | --- | --- |
| (2) | 2-Ethyl 1,2,3,4-tetrahydropyrrolo-[3,4-b]indole ethiodide | 3,3'-Thiodimethylenebis-(N,N-diethyl-1H-indole-2-methanamine) |
| (3) | 2-Methyl 1,2,3,4-tetrahydropyrrolo-[3,4,-b]indole ethiodide | 3,3'-Thiodimethylenebis-(N-ethyl-N-methyl-1H-indole-2-methanamine) |
| (4) | 2-Isopropyl 1,2,3,4-tetrahydropyrrolo-[3,4-b]indole isopropyl bromide | 3,3'-Thiodimethylenebis-(N,N-di-isopropyl-1H-indole-2-methanamine) |

I claim:
1. A compound of formula

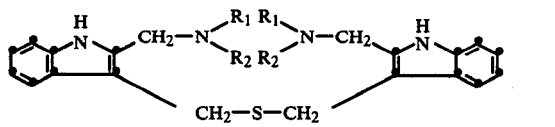

where $R_1$ and $R_2$ are lower alkyl groups and the corresponding pharmaceutically acceptable acid addition salts.

2. A compound according to claim 1 which is 3,3'-thiodimethylenebis(N,N-dimethyl-1H-indole-2-methanamine).

3. A compound according to claim 1 which is 3,3'-thiodimethylenebis(N,N-diethyl-1H-indole-2-methanamine).

4. A compound according to claim 1 which is 3,3'-thiodimethylenebis(N-ethyl-N-methyl-1H-indole-2-methanamine).

5. A compound according to claim 1 which is 3,3'-thiodimethylenebis(N,N-di-isopropyl-1H-indole-2-methanamine).

* * * * *